(12) United States Patent
Naft et al.

(10) Patent No.: US 6,770,045 B2
(45) Date of Patent: Aug. 3, 2004

(54) ORTHOSIS KNEE JOINT

(75) Inventors: Jonathan M. Naft, Chagrin Falls, OH (US); Wyatt S. Newman, Cleveland Heights, OH (US)

(73) Assignee: Becker Orthopedic Appliance Company, Troy, MI (US)

( * ) Notice: Subject to any disclaimer, the term of this patent is extended or adjusted under 35 U.S.C. 154(b) by 0 days.

(21) Appl. No.: 10/205,714

(22) Filed: Jul. 26, 2002

(65) Prior Publication Data

US 2002/0183673 A1 Dec. 5, 2002

Related U.S. Application Data

(63) Continuation of application No. 09/398,332, filed on Sep. 17, 1999, now Pat. No. 6,517,503.
(60) Provisional application No. 60/101,084, filed on Sep. 18, 1998.

(51) Int. Cl.[7] .................................................. A61F 5/00
(52) U.S. Cl. ............................ 602/16; 602/26; 600/592
(58) Field of Search ............................. 602/16, 23, 26; 128/882; 623/27, 39–46; 600/592

(56) References Cited

U.S. PATENT DOCUMENTS

| | | | | |
|---|---|---|---|---|
| 2,071,711 A | * | 2/1937 | Sprouls ........................ 623/41 |
| 2,485,036 A | * | 10/1949 | Christopher .................. 602/16 |
| 2,594,227 A | * | 4/1952 | Smith ........................... 623/44 |
| 2,700,772 A | * | 2/1955 | Davidson ..................... 623/41 |
| 2,943,622 A | * | 7/1960 | Nelson ......................... 602/16 |
| 4,520,804 A | * | 6/1985 | DiGeorge ..................... 602/16 |
| 4,745,930 A | | 5/1988 | Confer ......................... 128/779 |
| 4,760,850 A | | 8/1988 | Phillips et al. ............... 128/432 |
| 4,846,842 A | | 7/1989 | Connolly et al. |
| 5,010,774 A | | 4/1991 | Kikuo et al. |
| 5,045,829 A | | 9/1991 | Kuramochi et al. |
| 5,062,857 A | | 11/1991 | Berringer et al. |
| 5,121,742 A | * | 6/1992 | Engen .......................... 602/16 |
| 5,121,747 A | | 6/1992 | Andrews ..................... 128/423 |
| 5,133,774 A | | 7/1992 | Sawamura et al. |
| 5,253,656 A | | 10/1993 | Rincoe et al. |
| 5,257,673 A | | 11/1993 | Sato et al. |
| 5,267,950 A | | 12/1993 | Weddendorf |
| 5,282,460 A | | 2/1994 | Boldt .......................... 128/25 |
| 5,311,779 A | | 5/1994 | Teruo |
| 5,323,650 A | | 6/1994 | Fullen et al. |
| 5,328,446 A | | 7/1994 | Bunnell et al. ............... 602/16 |
| 5,408,873 A | | 4/1995 | Schmidt et al. ........ 73/862.625 |
| 5,490,831 A | * | 2/1996 | Myers et al. ................. 602/26 |
| 5,558,627 A | | 9/1996 | Singer et al. ................. 602/13 |
| 5,628,722 A | | 5/1997 | Solomonow ................. 602/26 |
| 5,662,693 A | | 9/1997 | Johnson et al. ............... 607/49 |
| 5,670,992 A | | 9/1997 | Yasuhara et al. |
| 5,678,448 A | | 10/1997 | Fullen et al. |
| 5,779,735 A | * | 7/1998 | Molino ........................ 623/44 |
| 5,808,540 A | | 9/1998 | Wheeler et al. |

(List continued on next page.)

OTHER PUBLICATIONS

Kenton K. Kaufman, et al., "Energy–Efficient Knee–Ankle-foot Orthosis: A Case Study," Journal of Prosthetics and Orthotics, vol. 8, No. 3 (1996), pp. 79–85.

"Foot Force Sensor," Cleveland Medical Devices Inc., Jul. 4, 1998.

Primary Examiner—Nicholas D. Lucchesi
Assistant Examiner—Tam Nguyen
(74) Attorney, Agent, or Firm—Ryndak & Suri (57) ABSTRACT

A selectively lockable orthotic joint is provided that in one embodiment includes at least one pressure sensor and an electronic circuit associated with the pressure sensor for generating or providing a control signal indicative of pressure, force or other value sensed by the sensor. A mechanical orthotic joint is provided that has a locking mechanism that can be selectively locked and unlocked in response to the control signal.

14 Claims, 7 Drawing Sheets

U.S. PATENT DOCUMENTS

| | | | |
|---|---|---|---|
| 5,976,063 A | 11/1999 | Joutras et al. | 482/114 |
| 5,977,959 A | 11/1999 | Katsurahira et al. | |
| 5,993,400 A | 11/1999 | Rincoe et al. | |
| 6,065,789 A | 5/2000 | Nagai et al. | |
| 6,174,294 B1 | 1/2001 | Crabb et al. | 600/592 |
| 6,188,229 B1 | 2/2001 | Nakamura | |
| 6,191,777 B1 | 2/2001 | Yasuhara et al. | |
| 6,316,646 B1 | 11/2001 | Tacke et al. | |
| 6,500,138 B1 * | 12/2002 | Irby et al. | 602/26 |
| 6,517,503 B1 * | 2/2003 | Naft et al. | 602/16 |
| 2002/0022508 A1 | 2/2002 | Ikariko | |
| 2002/0022518 A1 | 2/2002 | Okuda et al. | |

* cited by examiner

ORTHOSIS KNEE JOINT

CROSS REFERENCE TO RELATED APPLICATIONS

This is a continuation of U.S. patent application Ser. No. 09/398,332, filed Sep. 17, 1999, now U.S. Pat. No. 6,517,503, which claims the benefit under 35 U.S.C. §119 (e) of U.S. Provisional Application Serial No. 60/101,084, filed Sep. 18, 1998.

BACKGROUND OF THE INVENTION

This invention relates generally to orthoses for providing assistance in walking. More particularly, the present invention relates to an improved knee joint for such an orthosis.

An orthosis is a brace or other orthopedic device that is applied to a segment of a human body for the purpose of assisting in the restoration or improvement of its function. Orthoses can provide assistance in walking to persons having any of several types of walking disability. One known type of orthosis is a knee/ankle/foot orthosis which controls the motion and alignment of a knee and an ankle when a person attempts to walk. Such orthoses can be made of molded plastic materials or of metal and leather parts. Various knee and ankle joints can be added to achieve the desired function.

Typical reasons for wearing such an orthosis include stroke, brain injuries, spinal cord injury and post-polio treatment. A person who is not able to move his leg in a functional manner to ambulate, must wear a knee/ankle/foot orthosis to stabilize his leg and allow for ambulation. It has been found that for people with weak knee joints, a locking mechanism is necessary in order to lock a calf supporting orthosis to prevent movement in relation to a thigh supporting orthosis, thereby allowing the person to walk, albeit stiff legged.

There are many types of knee joints used on such orthoses. However, all the known joints which lock during ambulation are manual. In other words, when a patient is using the orthosis, he has a choice of walking with his leg locked in extension or in a free swing. If the patient chooses the locked position, he is forced to walk stiff legged. However, for some people, flexing at the knee during walking would result in a buckling of the person's leg. Therefore, walking stiff legged is much preferable to being not able to walk at all. Of course, a movement of the calf orthosis in relation to the thigh orthosis is necessary when the person decides to sit down.

As far as is known, there are no knee joints currently on the market which have the ability to automatically lock and unlock without direct manual patient intervention.

Accordingly, it has been considered desirable to develop a new and improved orthosis knee joint which would overcome the foregoing difficulties and others while providing better and more advantageous overall results.

BRIEF SUMMARY OF THE INVENTION

In accordance with the present invention, there is provided an orthosis for assistance in walking.

More particularly in accordance with this aspect of the invention, the orthosis includes an orthosis system which comprises a foot plate including at least one pressure sensor that senses the pressure exerted by a patient's foot on the foot plate, a circuit connected to at least one pressure sensor in the foot plate and a knee joint which is selectively locked and unlocked by the circuit. To this end, the knee joint is electrically operated.

More particularly mechanical orthotic joint of the selectively lockable orthotic joint invention includes an energizable electromagnetic coil, a spring washer deflectable in an axial direction when the electromagnetic coil is energized and an arrangement of first and second plates. The first plate has a face or an operative surface composed of a plurality of spaced teeth. The second plate also has a face or an operative surface having a plurality of spaced teeth that are complementary to the plurality of spaced teeth of the first plate. The second plate is mounted so that it is deflectable in an axial direction such that the plurality of spaced teeth of the second plate can engage the plurality of spaced teeth of the first plate when the electromagnetic coil is energized. The engagement of the first and second plates locks movement of the orthotic joint in at least one direction when the first and second plates are engaged.

More particularly, the mechanical orthotic joint of the selectively lockable orthotic joint invention includes an energizable electromagnetic coil, a spring washer is deflectable in an axial direction when the electromagnetic coil is energized and an arrangement of first and second plates. The first plate has a face or an operative surface composed of a plurality of spaced teeth. The second plate also has a face or an operative surface having a plurality of spaced teeth that are complementary to the plurality of spaced teeth of the first plate. The second plate is mounted so that it is deflectable in an axial direction such that the plurality of spaced teeth of the second plate can engage the plurality of spaced teeth of the first plate when the electromagnetic coil is energized. The engagement of the first and second plates locks movement of the orthotic joint in at least one direction when the first and second plates are engaged.

In accordance with one embodiment, the first and second plates are complementary and each comprise ratchet plates allowing the orthotic joint to move only in one direction when the joint is in a locked position. More specifically, in one embodiment, when unlocked the orthotic joint is movable in a flexion direction and an extension direction and when the orthotic joint is locked, it is movable only in the extension direction.

The first and second plates may comprise a low hysteresis magnetic material.

In accordance with another aspect of the present invention, a method for selectively locking and unlocking an orthotic joint is provided. One embodiment locks the orthotic joint to permit movement only in the extension direction.

In accordance with the method, an orthotic joint of the type previously described is utilized. Pressure is sensed by the pressure sensor and an electronic control signal is generated with the electronic circuit that is indicative of pressure sensed by the pressure sensor. In response to the electronic control signal, the orthotic joint locks through its locking mechanism.

One advantage of the present invention is the provision of a knee joint which allows patients, who are currently walking stiff legged with a locked knee joint in a knee/ankle/foot orthosis, to walk with a more normal gait.

Another advantage of the present invention is the provision of an orthosis which will make sitting and standing much safer and easier for any patient forced to manually unlock his knee joint.

Still another advantage of the present invention is the provision of an orthosis system which senses the pressure placed by a patient's foot on a foot plate of the orthosis and can automatically trigger a knee joint of the orthosis to lock and unlock. The knee joint will be locked when pressure is placed by the patient's foot on the foot plate. It will be unlocked when the patient's foot no longer exerts pressure on the foot plate.

In accordance with another aspect of the invention, a selectively lockable orthotic joint is provided. The selectively lockable orthotic joint includes an electronic circuit for providing at least one control signal indicative of a value. At least one mechanical orthotic joint is provided that includes a locking mechanism that is in communication with the circuit. The locking mechanism can be selectively locked and unlocked in response to the control signal. The control signal provided by the electronic circuit can originate from a variety of sources other than by sensing pressure or weight. For example, the control signal can originate from EMG signals in leg muscles, from EEG signals, from a sensor that detects distance between the ground and the bottom of a shoe or other article, such as a cane, for example. In addition, a controller could be provided for operation by the user, such as a joy stick or other type of switch in order to generate or otherwise provide the control signal for locking and/or unlocking the locking mechanism of the mechanical orthotic joint.

Still other benefits and advantages of the invention will become apparent to those of average skill in the art upon a reading and understanding of the following detailed specification.

BRIEF DESCRIPTION OF THE DRAWINGS

The invention may take physical form in certain parts and arrangements of parts, a preferred embodiment of which will be described in detail in this specification and illustrated in the accompanying drawings which form a part hereof and wherein.

DETAILED DESCRIPTION OF THE PREFERRED EMBODIMENT

Figures 12, 13:
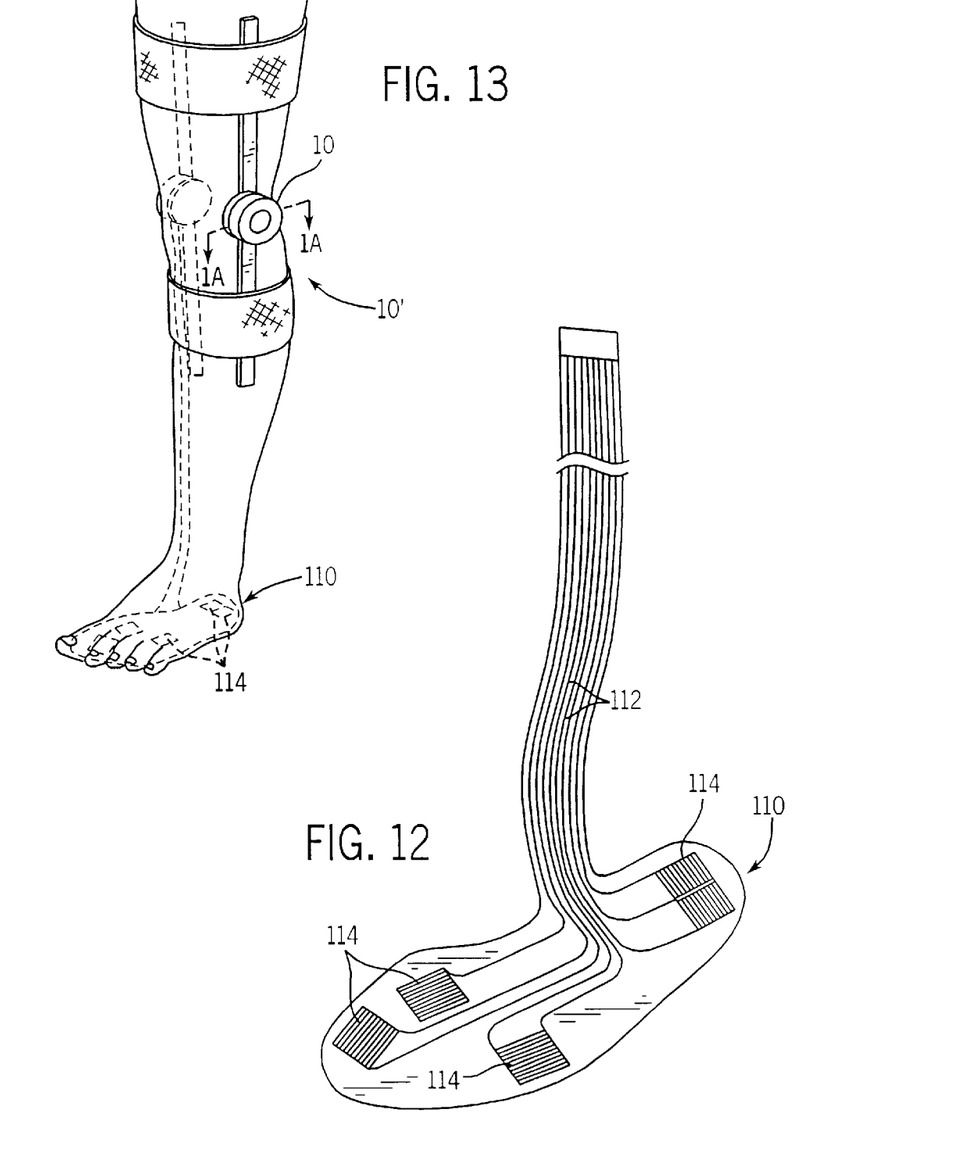
FIG. 12 is a perspective view of the force or pressure sensor employed with the joint of FIG. 1A.
FIG. 13 is a perspective view of an orthosis in accordance with the invention incorporating the joint of FIG. 1A and the sensor of FIG. 12.

Referring now to the drawings wherein the drawings are for purposes of illustrating a preferred embodiment of the invention only and not for purposes of limiting same, FIGS. 1A and 1B, 10 and 13, for example, show a knee joint 10 which is used in an orthosis 10' or orthopedic appliance, for example in FIG. 13. It is evident that two such knee joints would need to be employed for the two legs of a patient, one joint for each leg of the patient. Perhaps, even four knee joints could be used, one on either side of the knee of each leg of the patient. It is to be understood that joint 10 could be used other than as a knee joint, for example.

Figure 2A:
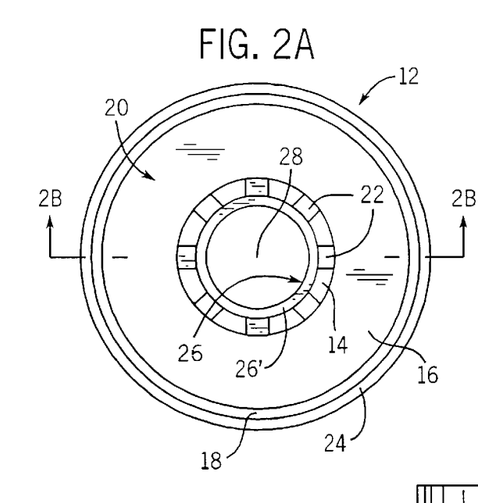
FIG. 2A is a top plan view of the toroidally shaped housing of the joint of FIG. 1A.
Figure 2B:
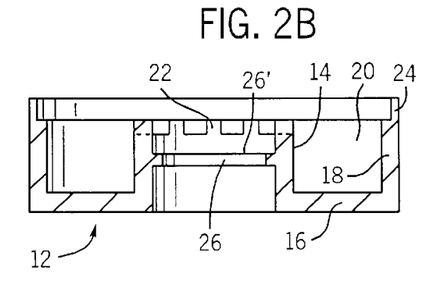
FIG. 2B is a cross-sectional view taken along line 2B—2B of FIG. 2A.

Joint 10 includes a toroidally shaped housing 12. Toroidally shaped housing 12 is depicted individually in FIGS. 2A and 2B. With reference now to FIGS. 2A and 2B, the toroidally shaped housing 12 has an inner wall 14, a base wall 16 and an outer wall 18 which together define a cavity 20. A plurality of spaced teeth 22 protrude upwardly from the inner wall 14. Preferably, eight such teeth are provided, although any suitable number of teeth can be utilized. A continuous flange 24 extends upwardly from the outer wall 18. A rib 26 extends radially inwardly from the inner wall 14 into a central opening 28 to form a toroidal ledge 26' approximately half way up the height of the inner wall.

Figure 3A:
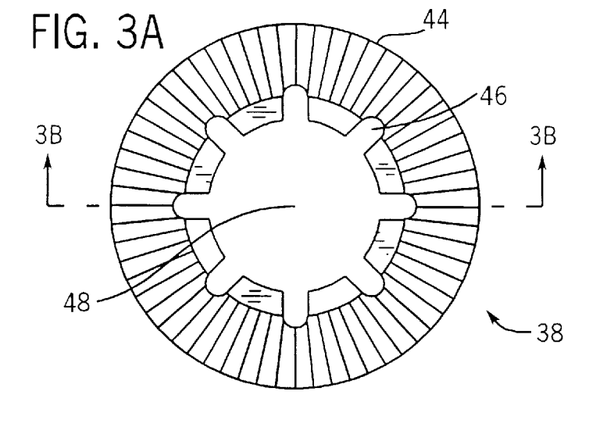
FIG. 3A is a top plan view of a bottom ratchet plate of the knee joint of FIG. 1A.
Figure 3B:
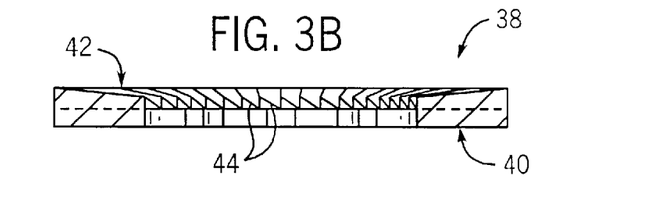
FIG. 3B is a side elevational view in cross section along line 3B—3B of FIG. 3A.

With reference again to FIGS. 1A and 1B and 10, an electromagnetic coil 30 is located in cavity 20. Electromagnetic coil 30 is formed around a plastic bobbin 32. Positioned on either side of rib 26 are a first bearing 34 and a second bearing 36. The bearings can be conventional roller bearings or other suitable bearings, as desired. A bottom ratchet plate 38 is also provided for the knee joint. Bottom ratchet plate 38 is depicted in greater detail FIGS. 3A and 3B. Bottom ratchet plate 38 includes a planar bottom surface 40, as illustrated in FIG. 3B, and a top face 42 having a plurality of radially extending spaced teeth 44 protruding therefrom. As is evident from FIG. 3A, sixty such teeth 44 are preferably located on the top face 42 with each tooth being spaced from the adjacent teeth by slots, although any suitable number of teeth can be utilized. Preferably, the teeth 44 are cut in a saw tooth pattern radially at a 30 degree slope. A set of eight spaced slots 46 are cut into the bottom ratchet plate 38. The slots extend radially outwardly from a central opening 48 of the plate 38 as is evident from FIG. 3A.

Figure 1A:
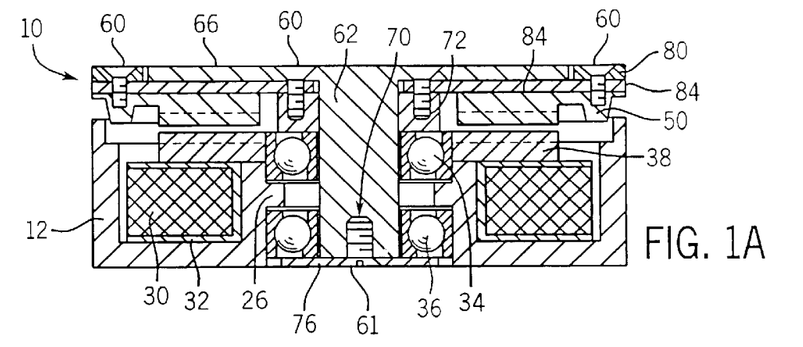
FIG. 1A is a side elevational view in cross section along line 1A—1A of FIG. 13 of a knee joint according to the present invention in an unlocked condition.
Figure 1B:
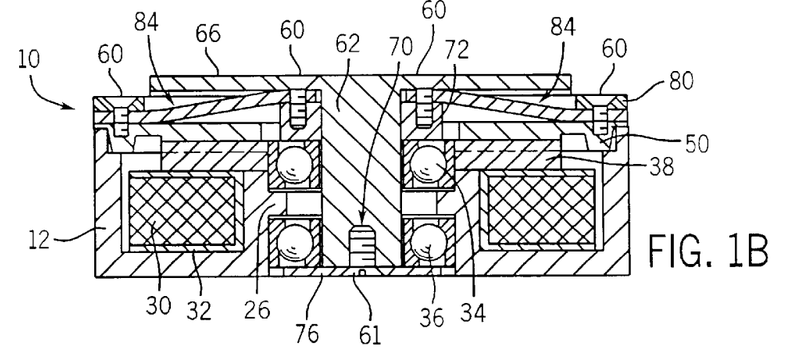
FIG. 1B is a side elevational view in cross section of the knee joint of FIG. 1A in a locked condition.
Figure 4A:
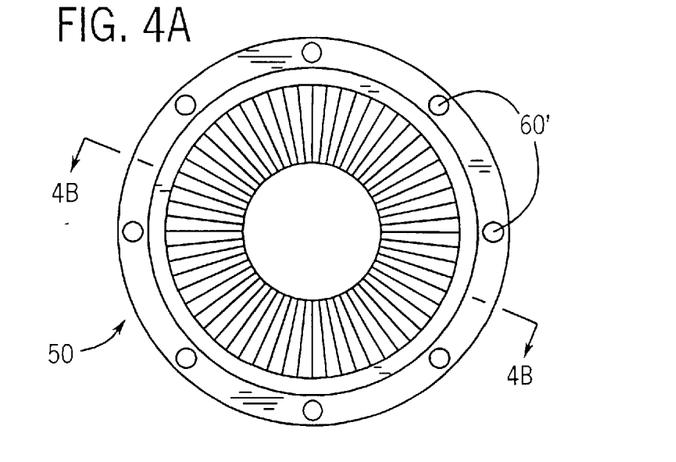
FIG. 4A is a bottom plan view of a top ratchet plate of the knee joint of FIG. 1A.
Figure 4B:
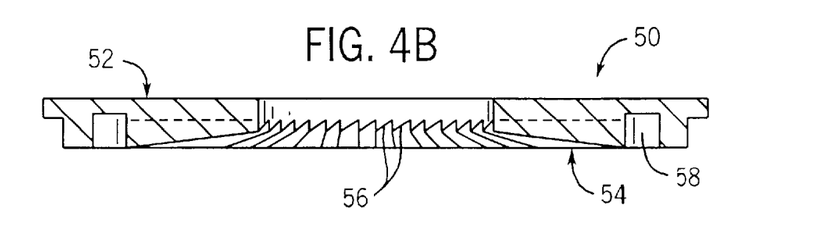
FIG. 4B is a side elevational view in cross section along line 4B—4B of FIG. 4A.

The joint of FIGS. 1A and 1B is further provided with a top ratchet plate 50, which is shown in more detail in FIGS. 4A and 4B. Top ratchet plate 50 is preferably constructed of a magnetically soft material, for example a low hysteresis, solenoid quality magnetic stainless steel. Bottom plate 38 may be constructed of similar material. With reference now to FIG. 4A, top ratchet plate 50 includes a top face 52 (FIG. 4B) and a bottom face 54. A plurality of spaced teeth 56 are cut into the bottom face 54. Preferably sixty such teeth are provided. As with the bottom plate 38, the teeth 56 in the top plate are cut in a saw tooth pattern radially at a 30 degree slope such that a tip of each tooth is separated from a tip of each adjacent tooth by 6 degrees. The teeth 56 of the top ratchet plate are meant to be and should be of suitable design and number to engage and mesh with the teeth 44 of bottom ratchet plate 38 when the two ratchet plates are brought into contact with each other. Also provided on top ratchet plate 50 is a slot 58 which circumscribes the teeth 56. A plurality of spaced apertures 60' extend through top ratchet plate 50. These apertures are positioned radially outwardly of slot 58. As is evident from FIGS. 1B and 10, suitable fasteners 60 can extend into the top ratchet plate apertures.

Figure 5A:
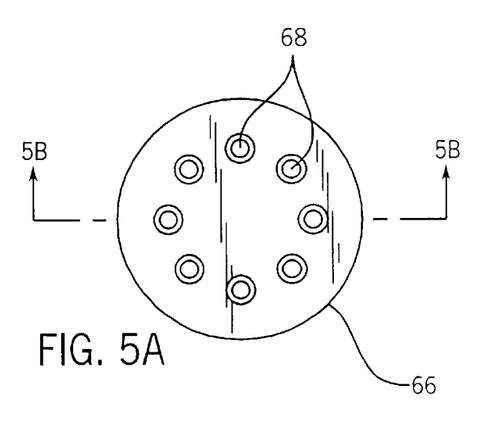
FIG. 5A is a top plan view of the top end portion of the knee joint of FIG. 1A.
Figure 5B:
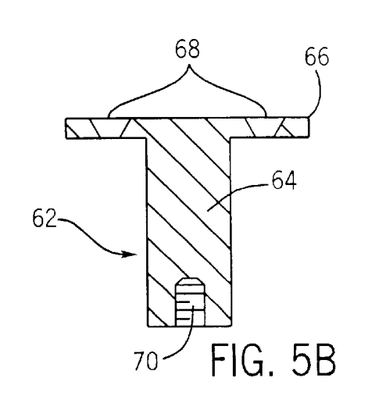
FIG. 5B is a side elevational view in cross section taken along line 5B—5B of FIG. 5A.
Figures 6, 6A, 7, 7A, 14, 15:
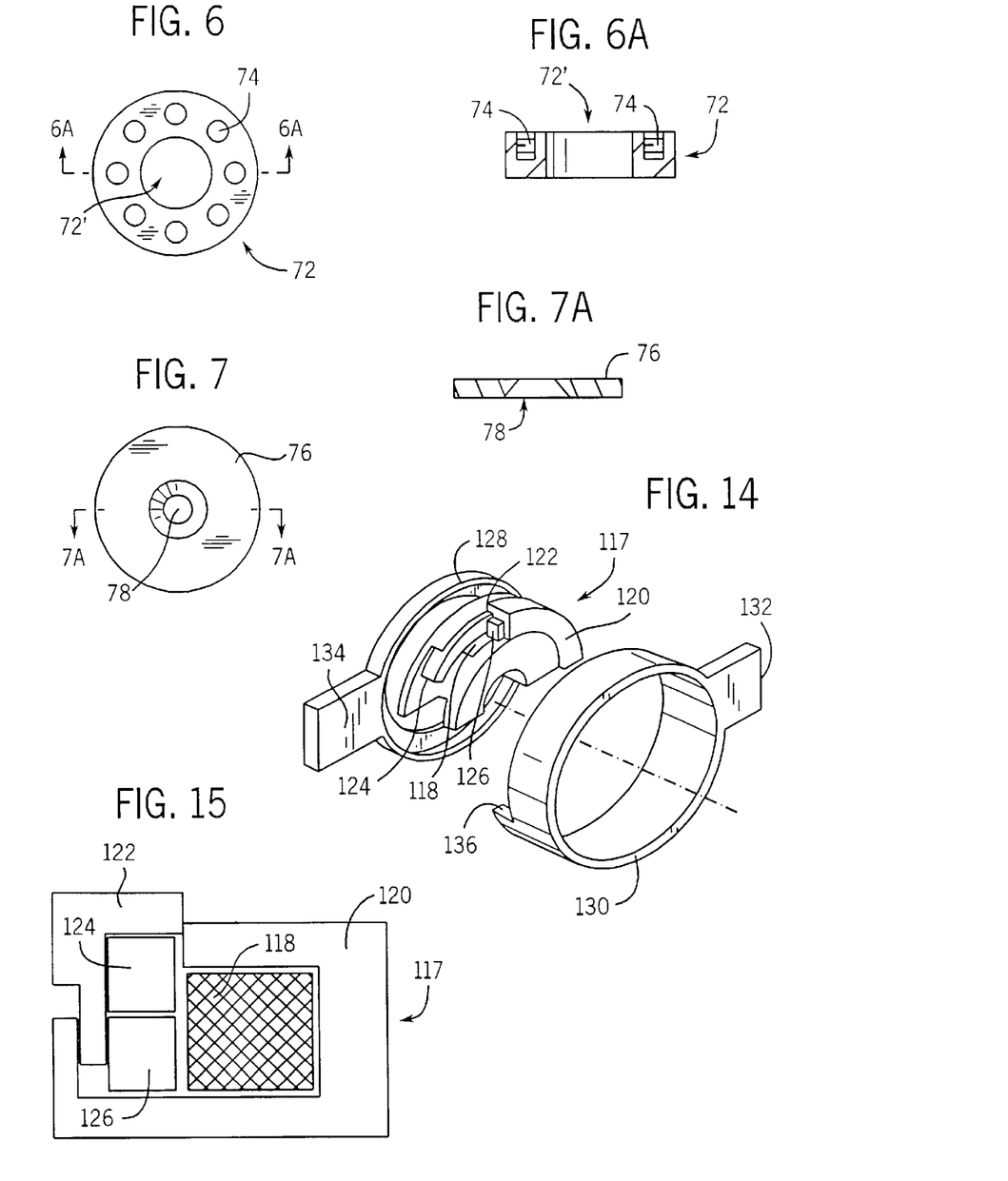
FIG. 6 is a top plan view of an inner retaining ring of the knee joint of FIG. 1A.
FIG. 6A is a cross-sectional view along lines 6A—6A of FIG. 6.
FIG. 7 is a top plan view of the retaining cap of the knee joint of FIG. 1A.
FIG. 7A is a cross-sectional view along line 7A—7A of FIG. 7.
FIG. 14 is a fragmentary perspective exploded view of an alternate embodiment joint in accordance with the invention.
FIG. 15 illustrates a cross-sectional schematic view of a portion of the alternate embodiment of FIG. 14.
Figure 10:
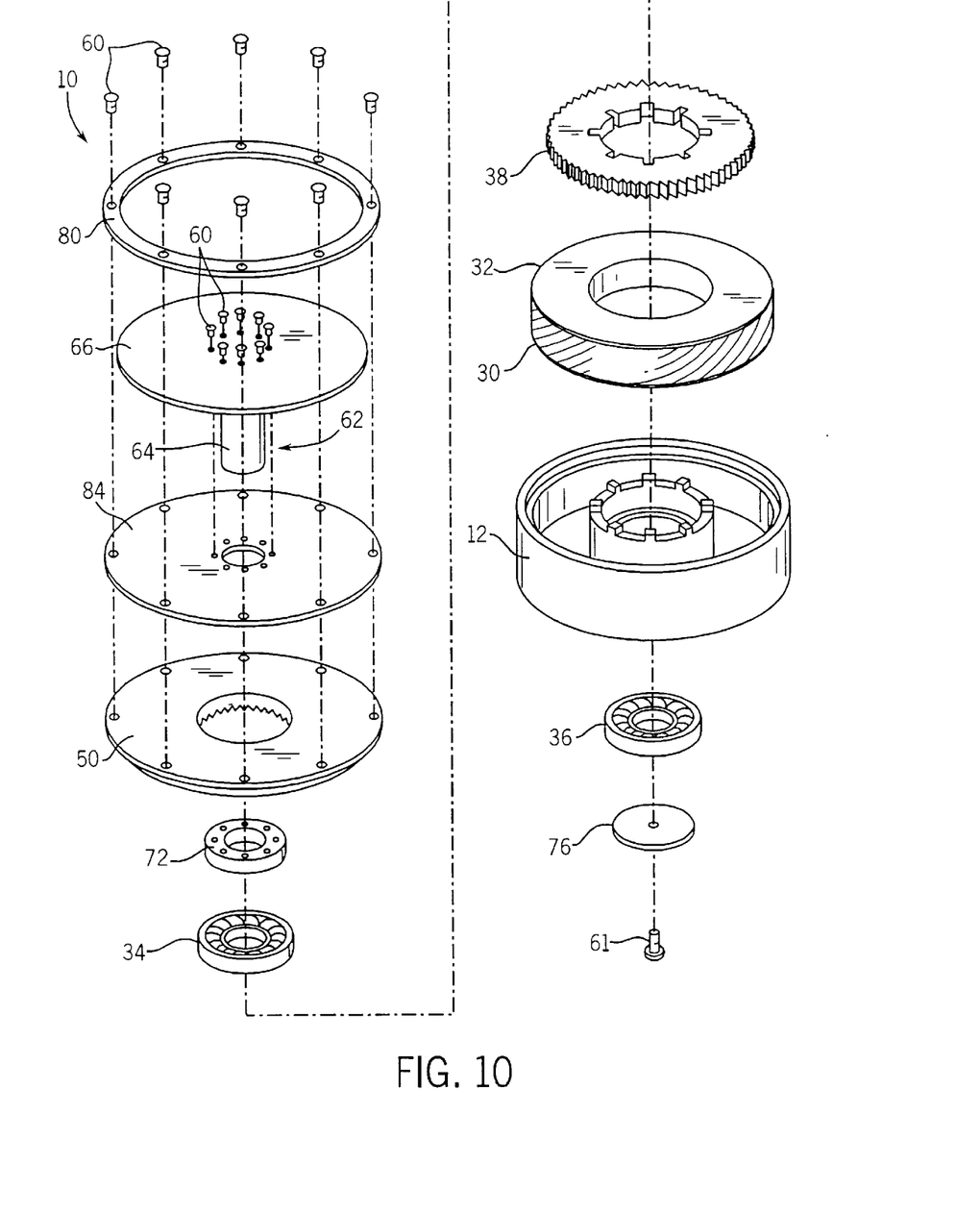
FIG. 10 is an exploded perspective view of components of the knee joint of FIG. 1A.

With reference now to FIGS. 1A, 1B and 10, a shaft 62 is also provided. As shown in FIGS. 5A and 5B shaft 62 includes a stem portion 64 and an enlarged top end 66 having a set of spaced apertures 68 extending therethrough. Note that in FIGS. 5A and 5B, the diameter of flange 66 is illustrated smaller than the diameter illustrated in the other figures. A bottom end of the stem portion 64 is provided with a centrally located aperture 70. Each of these apertures accommodates suitable fasteners 60 and 61. Referring to FIGS. 1A and 1B, also provided is an inner retaining ring 72. As detailed in FIG. 6, inner retaining ring 72 has a central aperture 72' for accommodating stem portion 64 and includes a set of apertures 74 extending therein. Each of apertures 74 is also meant to accommodate a suitable fastener 60. A retaining cap 76 is also provided. As shown in FIGS. 7 and 7A, retaining cap 76 has a centrally extending aperture 78 for accommodating a suitable fastener 61. Fasteners 60 and 61 can be threaded fasteners or any other suitable type of fastener, for example.

Figure 8:
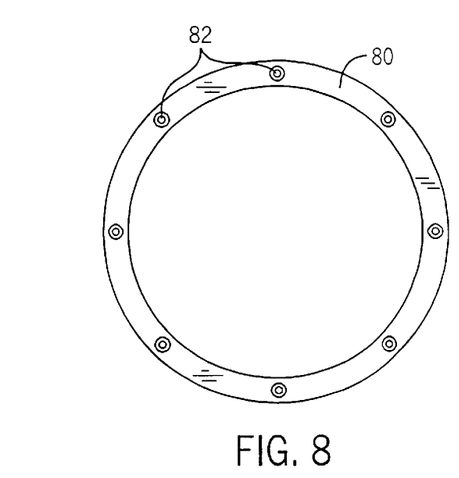
FIG. 8 is a top plan view of an outer retaining ring of the joint of FIG. 1A.

Joint 10 is also provided with an outer retaining ring 80. As shown in FIG. 8 a set of apertures 82 extend through retaining ring 80 to accommodate suitable fasteners 60. As shown in FIGS. 1A, 1B, 9 and 10, a spring washer 84 is further provided. Spring washer 84 is preferably comprised of a plurality of very thin pieces of metal which, when assembled, is very compliant in an axial direction while maintaining a high rigidity in torsion. For example, spring washer 84 may consist of approximately 60 pieces of 0.001 inch thick stainless steel disks. The axial compliance allows the spring washer to be deflected at relatively low electromagnetic forces allowing the upper ratchet plate to mesh with the lower ratchet plate. Spring washer 84, further depicted in FIG. 9, has a set of outer apertures 86 for accommodating a suitable first set of fasteners 60 and a set of inner apertures 88 similarly for accommodating a suitable second set of fasteners 60. Spring washer 84 also has a central opening 90 to accommodate stem portion 64 of shaft 62.

Figure 9:
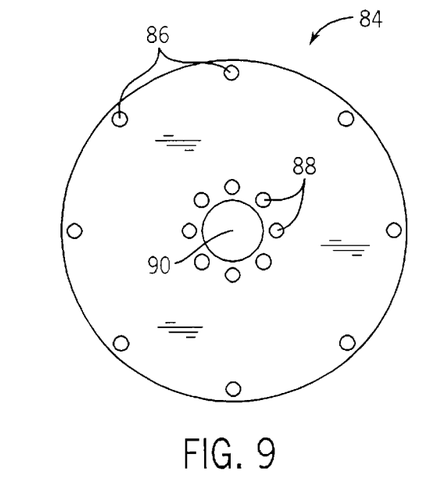
FIG. 9 is a top plan view of a spring washer of the joint of FIG. 1A.

Spring washer 84 is very compliant in the axial direction, permitting deflection of upper ratchet plate 50 even with relatively low electromagnetic attraction forces, typically deflecting about $1/16^{th}$ of an inch in an axial direction with an electromagnetic force of several pounds. Thus, the significant axial deflection that is obtained with low electromagnetic forces permits operation of joint 10 at low power consumption levels which is important for battery-operated use. Spring washer 84, however, is strong and stiff in torsion, providing the necessary reaction torque to support the moments required in an orthotic application. Any suitable washer that performs the function of spring washer 84 can be utilized in accordance with the invention.

As is evident from FIGS. 1A, 1B and 10, shaft 62 is located in central opening 28 of toroidally shaped housing 12. Retaining cap 76 is fastened to shaft 62 by fastener 61. In this way, two bearings 34 and 36 can be secured in place in central opening 28 of housing 12. Bottom ratchet plate 38 is seated on inner wall 14 of housing 12. To this end, several spaced slots 46 in bottom ratchet plate 38 accommodate several spaced teeth 22 in housing 12. More particularly, eight slots 46 and eight teeth 22 are provided in housing 12. It is apparent that no keying is necessary since bottom ratchet plate 38 can be rotated in relation to the housing to any desired extent so long as the slots 46 are aligned with teeth 22.

Top ratchet plate 50 is positioned above bottom ratchet plate 38. In the condition illustrated in FIG. 1A, top ratchet plate 50 is spaced from bottom ratchet plate 38. This allows a movement of joint 10 in either rotational direction (flexion or extension). In the position illustrated in FIG. 1B, the teeth of top ratchet plate 50 engage the teeth of bottom ratchet plate 38 to prevent any further rotation of the joint. Preferably, the two ratchet plates are spaced from each other as indicated when in the unactuated state as shown in FIG. 1A.

With reference again to FIG. 1A, spring washer 84 is fastened to flange 66 of shaft 62 via inner retaining ring 72. Spring washer 84 is also fastened to top ratchet plate 50 and outer retaining ring 80 by fasteners 60. In this way, top ratchet plate 50 is normally spring-biased away from bottom ratchet plate 38. However, top ratchet plate 50 is pulled into contact with bottom ratchet plate 38 when electromagnetic current is flowing through electromagnetic coil 30.

Figure 11:
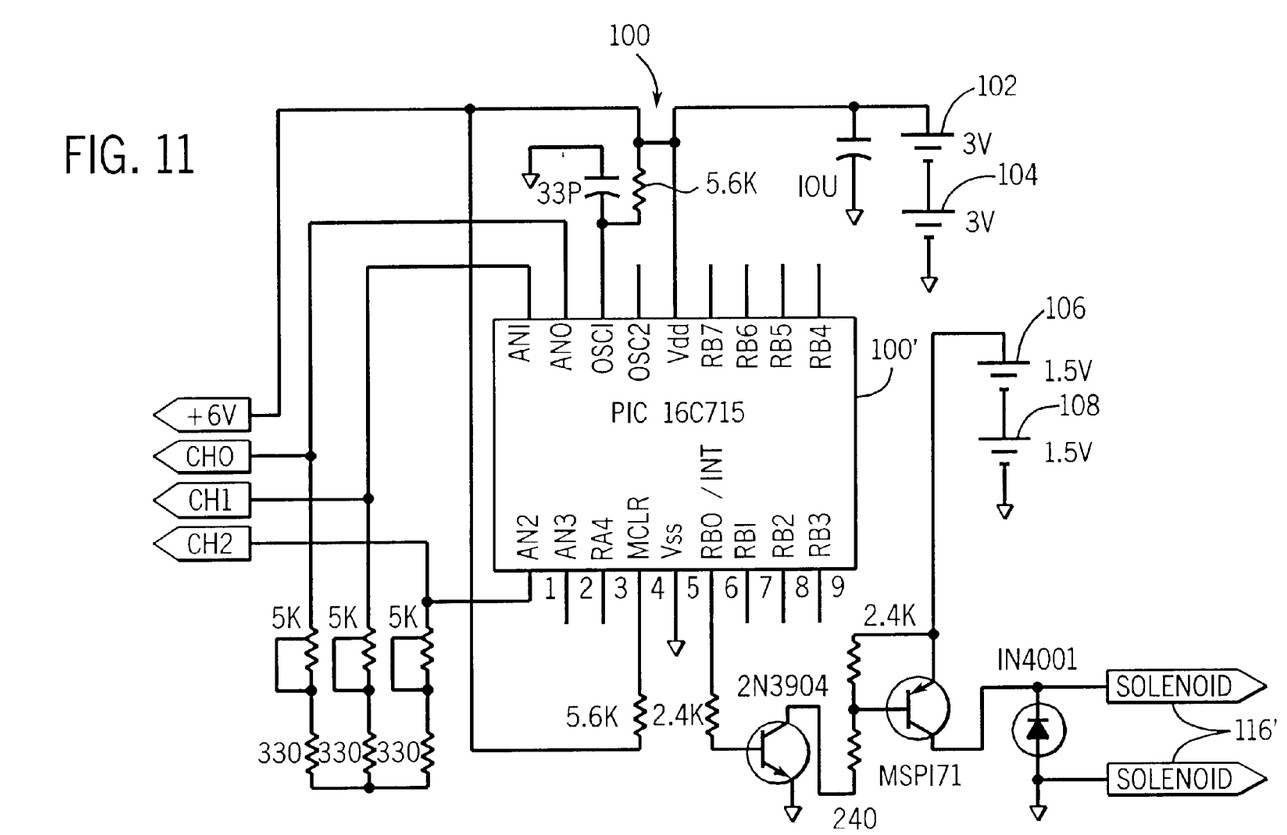
FIG. 11 is a circuit diagram of a circuit which is employed with the knee joint of FIG. 1A and the force or pressure sensor of FIG. 12.

With reference now to FIG. 11, a circuit 100 which includes an integrated circuit 100', which can be a Microchip Model No. PIC16C715, is employed to control the operation of joint 10. The integrated circuit is preferably powered by a pair of 3 volt batteries 102 and 104. Electromagnetic coil 30 is preferably powered by a pair of 1.5 volt batteries 106 and 108.

With reference now to FIG. 12, an insole pressure or foot force sensor 110 is also used in connection with the joint 10. More particularly, a set of output lines 112 lead from a set of sensors 114 in the insole to circuit 100. Batteries 102 and 104 provide a reference signal for the sensors. A pair of output lines 116' from circuit 100 extend to the electromagnetic coil 30. The pair of 1.5 volt batteries 106 and 108, which are of relatively higher power than the power of the 3 volt batteries, are meant to power the electromagnetic coil.

Insole pressure sensor 110 is preferably provided with five sensors which detect pressure by a voltage drop across very thin resistors, for example the foot force sensor provided by Cleveland Medical Devices, Inc. It should be apparent to one skilled in the art that more or less sensors may be used. The insole is slipped inside a patient's shoe. The signal from the insole is translated through wires 112 to circuit 100. Integrated circuit 100' also contains a programmable microprocessor. Any suitable microprocessor can be utilized. The processor determines a threshold level and sends a signal to the joint 10 attached to a knee joint as depicted in FIG. 13. However, the joint need not be limited to a knee joint, but may also be an ankle, wrist or elbow joint. Any suitable pressure or force sensor can be used in accordance with the invention.

With the orthosis of the present invention, when a person puts his foot on the floor, the sensors 114 in insole sensor 110 sense a pressure and can trigger the joint 10 to lock by energizing electromagnetic coil 30 thereby bringing the top ratchet plate 50 down into contact with bottom ratchet plate 38 engaging respective teeth 56 and 44. Preferably, this action prevents any further rotation of the joint in one rotational direction, however, this may lock the joint entirely from rotating. More particularly, top ratchet plate 50 and shaft 62 cannot rotate via bearings 34 and 36 in relation to bottom ratchet plate 38 and housing 12 toward a bent knee position. Preferably, when the teeth of the upper and lower ratchet plates are engaged, the joint allows incremental slip (ratcheting) in a joint extension. However, when no more pressure is sensed by sensors 114 of the insole sensor 110, circuit 100 will unlock the knee joint by ceasing the flow of electric current in the electromagnetic coil.

Once this occurs, spring washer 84 will pull top ratchet plate 50 out of engagement with bottom ratchet plate 38. This will allow a rotation of the knee joint in both directions. In particular, top ratchet plate 50 and shaft 62 are again capable of rotating in relation to bottom ratchet plate 38 and housing 12. Thus, the joint is unlocked when pressure of the patient's foot is no longer exerted on the insole sensor 110. This invention will allow a user who is currently wearing stiff legged knee/ankle/foot orthoses to walk with a more normal gait. In addition, it will make sitting and standing safer and easier for any user currently forced to manually unlock their knee joint.

When a threshold level is reached, a magnetic field is generated by electromagnetic coil 30 to pull top ratchet plate 50 into engagement with bottom ratchet plate 38, no longer allowing the two ratchet plates to rotate freely in relation to each other. This locks the knee joint and prevents it from bending into flexion. However, the joint will still allow extension. As an example, if the patient is attempting to stand and gets stuck halfway up, the joint will block flexion and prevent the patient's knee from buckling. But, it will still ratchet into extension and allow the patient to continue moving vertically. Thus, a very important advantage of the present invention is the provision of a knee joint in which flexion is prevented when the top ratchet plate 50 meshes with bottom ratchet plate 38 but extension is still allowed. This is accomplished due to the orientation of the meshing teeth 44 and 56 of the bottom and top ratchet plates 38 and 50.

As a second example, a user, when he takes a step, will have the insole read the floor contact and lock the knee for the user. The knee remains locked through the step and then unlocks when the user initiates swing through, i.e. takes the pressure off the first leg and puts the pressure on the second leg. The knee joint will then lock again at the next initial floor contact.

Sensors 114 could be wired in series or in parallel for the signal which is sent through wires 112 to circuit 100. Preferably, the output of all of sensors 114 is summed together. If a set point is reached, electromagnetic coil 30 is triggered and the knee joint is locked. However, the logic of the chip on the integrated circuit could be programmed to differentiate between, e.g. a heel strike and a toe strike of the foot plate. The logic of the circuit may also provide that given patterns of pressure, for example placing pressure on only inner or outer pressure sensors, detected by the sensors could disengage the teeth in the joint permitting an individual to sit.

Joint 10 according to the present invention can be attached to any conventional knee/ankle/foot/elbow/wrist orthosis or any knee brace as long as the brace is fabricated to the joint size specification. A person skilled in the art should realize that the orthotic joint of the present invention supports passive locking arrangements wherein the joint is locked until the coil is magnetized which unlocks the joint as opposed to the active locking embodiment of the joint as described above.

FIGS. 14 and 15 illustrate an alternate embodiment of an electronically controlled orthotic joint according to the present invention. This embodiment as shown in FIGS. 14 and 15 provides an electromagnetic coil 118 located within a housing 120. Actuating portion 122 is provided as well as opposing teeth inserts 124 and 126. Engagement of the teeth inserts 124 and 126 is actuated by energizing coil 118. The coil is energized under control of a microprocessor (not shown) as in the above embodiment. Energizing the coil produces an axial force on actuating portion 122 which forces teeth insert 124 into engagement with teeth insert 126. In this embodiment, a passive spring (not shown) causes the teeth of teeth inserts 124 and 126 to disengage upon interruption of current through coil 118. This embodiment can also provide for incremental slip in a single rotational direction as desired. Further, teeth inserts 124 and 126 are constructed of non-magnetic material so that they may be made of a more durable material, for example tool steel. This embodiment also provides a spline interface (not shown) between outer support ring 130 and actuating element 122. This spline interface is on the internal surface of outer support ring 130 and the external surface of actuating element 122. This spline interface permits axial translation of actuating element 122 while enabling large torques to be transmitted from outer support ring 130 to actuating element 122. This arrangement permits application of large torques from outer support ring 130 to the opposite outer support ring 128 as follows. Torques are transmitted from element 130 to element 122 via the spline interface. Torques are thus transmitted from actuator element 122 to teeth insert 124, which is fastened rigidly to element 122. When engaged due to actuation (axial translation of element 122), teeth insert 124 meshes with teeth insert 126 enabling transmission of torques that oppose knee flexion. Teeth insert 126, rigidly fastened to housing 120, transmits torques to housing 120 via its fasteners. Finally, housing 120, which is rigidly fastened to outer support ring 128, transmits torque to outer support ring 128 via fasteners (not shown). In this manner, torques can be transmitted from support arm 132 of outer support ring 130 to support arm 134 of the opposite outer support ring 128. Support arms 132 and 134 provide a convenient structure to mechanically interface the locking mechanism to orthotic bracing. One skilled in the art should recognize that an equal and opposite torque is transmitted to outer support ring 128 and support arm 134 in a similar manner.

FIG. 14 depicts how joint 117 is integrated into an orthotic device. Outer support rings 128 and 130 house joint 117. As shown in FIG. 14, joint 117 is comprised of an electromagnetic coil 118, housing 120, actuating portion 122, and teeth inserts 124 and 126. The outer support rings are constructed of non-magnetic metallic material. Outer support ring 130 has an attached support arm 132 which attaches to a limb portion of a patient. Similarly, outer support ring 128 has a support arm 134 that attaches to the same limb portion of a patient as support arm 132, but joint 117 is aligned with the patient's joint which is to be supported.

While the invention has been described with respect to certain preferred embodiments, as will be appreciated by those skilled in the art, it is to be understood that the invention is capable of numerous changes, modifications and alterations that are within the scope of the appended claims.

What is claimed is:

1. A selectively lockable orthotic device for association with the leg of a person comprising:

a selectively lockable mechanical orthotic knee joint that is capable of flexion and extension movement and includes a rigid locking mechanism having at least two axially opposed plates with intermeshing teeth, said rigid locking mechanism preventing flexion but permitting extension when in a locked position and permitting flexion and extension when in an unlocked position;

a pressure sensor for sensing a threshold pressure exerted by the person's foot that is indicative of a person placing at least a portion of his weight on the leg associated with the device; and an electronic control circuit for controlling the rigid locking and unlocking of said plates that causes the knee joint to be in a locked position when at least the threshold pressure is placed on the foot of the person and sensed by the pressure sensor and in an unlocked position when less than the threshold pressure is placed on the person's foot and sensed by the pressure sensor.

2. The selectively lockable orthotic device of claim 1 wherein said plates are toroidal in shape.

3. The selectively lockable orthotic device of claim 1 wherein the intermeshing teeth of said plates interlock when in the locked position.

4. The selectively lockable orthotic device of claim 1 wherein the axially opposed plates are spaced apart in the unlocked position.

5. The selectively lockable orthotic device of claim 1 wherein at least one plate is deflectable in an axial direction.

6. The selectively lockable orthotic device of claim 4 wherein at least one plate is made of a low hystereris material.

7. The selectively lockable orthotic device of claim 1 wherein the pressure sensor is selected from the group consisting of a heel pressure sensor, a toe area pressure sensor, a midfoot area pressure sensor and combinations thereof.

8. A selectively lockable orthotic device for association with the leg of a person comprising:

a selectively lockable mechanical orthotic knee joint that is capable of flexion and extension movement and includes means for rigidly locking the knee joint to prevent flexion and to permit extension of the knee joint when the knee joint is in a locked position and which locking mechanism permits flexion and extension of the knee joint when the knee joint is in an unlocked position;

a sensor for sensing a threshold control signal from the person's leg that is indicative of a person placing at least a portion of his weight on the leg associated with the device; and an electronic control circuit for controlling the rigid locking and unlocking of the knee plates that causes the knee joint to be in a locked position when at least the threshold signal is sensed by the sensor and in an unlocked position when less than the threshold signal is sensed by the sensor.

9. The selectively lockable orthotic device of claim 8 wherein said control sign is an EMG signal.

10. A method for selectively locking and unlocking an orthotic device associated with a leg of a person comprising a selectively lockable orthotic joint having at least one pressure sensor, an electronic circuit associated with said pressure sensor for controlling the orthotic joint, the orthotic joint having a rigid locking mechanism having at least two axially opposed plates with intermeshing teeth, the locking mechanism selectively locked allowing extension and preventing flexion and unlocked allowing extension and flexion in response to the sensed pressure, the method comprising:

sensing pressure exerted by the person's foot with the pressure sensor that communicates with the electronic circuit; and interlocking the intermeshing teeth of the axially opposed plates with the electronic circuit when at least a threshold pressure is sensed by the sensor.

11. The method of claim 10 further comprising disengaging the axially opposed plates with the electronic circuit when less than the threshold pressure is sensed by the sensor.

12. The method of claim 10 wherein said interlocking prevents flexion movement and permits extension movement.

13. The method of claim 11 wherein said disengaging permits flexion and extension movement.

14. The method of claim 10 wherein said sensing occurs during walking, standing, moving from a standing to a seated position, or moving from a seated to a standing position.

* * * * *